United States Patent [19]

Franke et al.

[11] 4,340,595
[45] Jul. 20, 1982

[54] AMINOPROPANOL DERIVATIVES OF 6-HYDROXY-2,3,4,5-TETRAHYDRO-1H-1-BENZAZEPIN-2-ONE AND PHARMACEUTICAL FORMULATIONS CONTAINING THE SAID COMPOUNDS

[75] Inventors: Albrecht Franke, Wachenheim; Dieter Lenke, Ludwigshafen; Josef Gries, Wachenheim; Hans D. Lehmann, Hirschberg-Leutershausen, all of Fed. Rep. of Germany

[73] Assignee: BASF Aktiengesellschaft, Fed. Rep. of Germany

[21] Appl. No.: 226,485

[22] Filed: Jan. 19, 1981

Related U.S. Application Data

[63] Continuation of Ser. No. 91,200, Nov. 7, 1979, abandoned.

[30] Foreign Application Priority Data

Nov. 18, 1978 [DE] Fed. Rep. of Germany ....... 2850078

[51] Int. Cl.³ .................... A61K 31/55; C07D 223/16
[52] U.S. Cl. .............................. 424/244; 260/239.3 B
[58] Field of Search .................. 260/239.3 B; 424/244

[56] References Cited

PUBLICATIONS

Shtacher et al., "J. Med. Chem.", vol. 16, No. 5, pp. 516–519 (1973).
Nakagawa et al., "J. Med. Chem.", vol. 17, No. 5, pp. 529–532 (1974).
Erez et al., "J. Med. Chem.", vol. 21, No. 9, pp. 982–984 (1978).
Handbook of Experimental Pharmacology (Springer-Verlag) (1977), Oates et al., pp. 598–599.
Japan J. Pharmacol., vol. 24, pp. 853–861, (1974) Yabuuchi et al.
Japan J. Pharmacol., vol. 24, pp. 863–868, (1974) Sasa et al.

Primary Examiner—Robert T. Bond
Attorney, Agent, or Firm—Keil & Witherspoon

[57] ABSTRACT

Aminopropanol derivatives of 6-hydroxy-2,3,4,5-tetrahydro-1-H-1-benzazepin-2-one of the formula

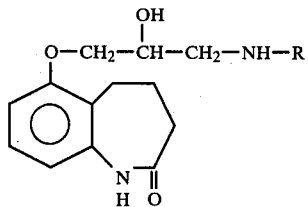

where R is alkyl of 1 to 6 carbon atoms, which is unsubstituted or substituted by hydroxyl or by alkoxy of 1 to 3 carbon atoms, or is alkenyl or alkynyl of 3 to 6 carbon atoms or is cycloalkyl of 3 to 7 carbon atoms in the ring, and their physiologically acceptable addition salts with acids, their preparation and pharmaceutical formulations, containing the said compounds, which because of their β-sympatholytic action can be used as cardiac and circulatory drugs.

4 Claims, No Drawings

AMINOPROPANOL DERIVATIVES OF 6-HYDROXY-2,3,4,5-TETRAHYDRO-1H-1-BENZAZEPIN-2-ONE AND PHARMACEUTICAL FORMULATIONS CONTAINING THE SAID COMPOUNDS

This is a continuation, of application Ser. No. 091,200, filed Nov. 7, 1979 now abandoned.

The present invention relates to novel aminopropanol derivatives of 6-hydroxy-2,3,4,5-tetrahydro-1H-1-benzazepin-2-one and their addition salts with acids, as well as to the preparation of these compounds and to pharmaceutical formulations containing the said compounds.

It is known, for example, that aminopropanol derivatives of 7-hydroxy-2,3,4,5-tetrahydro-1H-2-benzazepin-1-one (J. Med. Chem. 16 (1973), 516–519), of 5-hydroxy-3,4-dihydrocarbostyril (J. Med. Chem. 17 (1974), 529–533) and of 7-hydroxy-2,3,4,5-tetrahydro-1H-1-benzazepin-2-one (J. Med. Chem. 21 (1978), 928–984) exhibit β-sympatholytic effects.

We have found that compounds of the general formula (I)

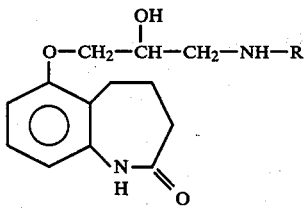

where R is alkyl of 1 to 6 carbon atoms, which is unsubstituted or substituted by hydroxyl or by alkoxy of 1 to 3 carbon atoms, or is alkenyl or alkynyl of 3 to 6 carbon atoms, or is cycloalkyl of 3 to 7 carbon atoms in the ring, and their physiologically acceptable addition salts with acids, exhibit a higher pharmacological activity.

Examples of alkyl of 1 to 6 carbon atoms, which may be straight-chain or branched, are methyl, ethyl, propyl, isopropyl, n-butyl, isobutyl, sec.-butyl, tert-butyl, pent-2-yl, 2-methyl-but-2-yl, 3-methyl-but-2-yl, 3-methyl-pent-3-yl and 2,3-dimethyl-but-2-yl, and examples of substituted alkyl are 1-methoxy-prop-2-yl, 2-hydroxyeth-1-yl, 1-hydroxy-but-2-yl and 3-hydroxy-3-methyl-but-1-yl.

Amongst alkyl radicals, those branched at the carbon in the α-position to the amino nitrogen are preferred. Accordingly, preferred alkyl radicals are isopropyl, tert.-butyl, sec.-butyl, 2-methylbut-2-yl, 3-methylpent-3-yl and pent-2-yl. Possible substituents of the preferred alkyl radicals are, in particular alkoxy of 1 to 3 carbon atoms, especially methoxy, so that an example of such a substituted radical is 1-methoxy-prop-2-yl.

Examples of alkenyl or alkynyl radicals of 3 to 6 carbon atoms are prop-1-en-3-yl, but-3-yn-2-yl, 2-methyl-but-3-yn-2-yl and 3-methyl-pent-1-yn-3-yl. Amongst these, alkynyl radicals, eg. but-3-yn-2-yl and 3-methyl-but-1-yn-2-yl, are preferred.

Examples of cycloalkyl radicals are cyclopropyl, cyclobutyl, cyclopentyl and cyclohexyl, amongst which cyclopropyl is preferred.

Accordingly, examples of compounds according to the invention, of the formula (I), are: 6-(2-hydroxy-3-methylaminopropoxy)-2,3,4,5-tetrahydro-1H-1-benzazepin-2-one, 6-(2-hydroxy-3-ethylaminopropoxy)-2,3,4,5-tetrahydro-1H-1-benzazepin-2-one, 6-(2-hydroxy-3-n-propylaminopropoxy)-2,3,4,5-tetrahydro-1H-1-benzazepin-2-one, 6-(2-hydroxy-3-isopropylaminopropoxy)-2,3,4,5-tetrahydro-1H-1-benzazepin-2-one, 6-(2-hydroxy-3-n-butylaminopropoxy)-2,3,4,5-tetrahydro-1H-1-benzazepin-2-one, 6-(2-hydroxy-3-sec.-butylaminopropoxy)-2,3,4,5-tetrahydro-1H-1-benzazepin-2-one, 6-(2-hydroxy-3-tert.-butylaminopropoxy)-2,3,4,5-tetrahydro-1H-1-benzazepin-2-one, 6-[2-hydroxy-3-(2-methylbutyl-2-amino)-propoxy]-2,3,4,5-tetrahydro-1H-1-benzazepin-2-one, 6-[2-hydroxy-3-(2,3-dimethylbutyl-2-amino)-propoxy]-2,3,4,5-tetrahydro-1H-1-benzazepin-2-one, 6-[2-hydroxy-3-(pentyl-2-amino)-propoxy]2,3,4,5-tetrahydro-1H-1-benzazepin-2-one, 6-(2-hydroxy-3-cyclopropylamino-propoxy)-2,3,4,5-tetrahydro-1H-1-benzazepin-2-one, 6-(2-hydroxy-3-cyclopentylamino-propoxy)-2,3,4,5-tetrahydro-1H-1-benzazepin-2-one, 6-(2-hydroxy-3-cyclohexylamino-propoxy)-2,3,4,5-tetrahydro-1H-1-benzazepin-2-one, 6-[2-hydroxy-3-(1-methoxypropyl-2-amino)-propoxy]-2,3,4,5-tetrahydro-1H-1-benzazepin-2-one, 6-[2-hydroxy-3-(2-hydroxyethylamino)-propoxy]-2,3,4,5-tetrahydro-1H-1-benzazepin-2-one, 6-[2-hydroxy-3-(prop-1-en-3-ylamino)-propoxy]-2,3,4,5-tetrahydro-1H-1-benzazepin-2-one, 6-[2-hydroxy-3-(but-1-yn-3-ylamino)-propoxy]-2,3,4,5-tetrahydro-1H-1-benzazepin-2-one and 6-[2-hydroxy-3-(3-methy-but-1-yn-3-ylamino)-propoxy]-2,3,4,5-tetrahydro-1H-1-benzazepin-2-one.

The following compounds are preferred: 6-(2-hydroxy-3-isopropylaminopropoxy)-2,3,4,5-tetrahydro-1H-1-benzazepin-2-one, 6-(2-hydroxy-3-sec.-butylaminopropoxy)-2,3,4,5-tetrahydro-1H-1-benzazepin-2-one, 6-(2-hydroxy-3-tert.-butylaminopropoxy)-2,3,4,5-tetrahydro-1H-1-benzazepin-2-one and 6-[2-hydroxy-3-(3-methyl-but-yn-3-ylamino)-propoxy]-2,3,4,5-tetrahydro-1H-1-benzazepin-2-one.

To prepare a compound according to the invention of the formula (I), a 2,3,4,5-tetrahydro-1H-1-benzazepin-2-one of the general formula (II)

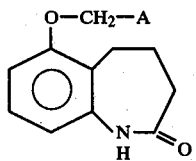

where A is

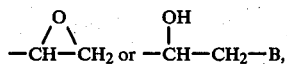

B being a nucleofugic leaving group, is reacted, in the conventional manner with an amine of the general formula

where R has the above meanings, advantageously in a solvent, and in the presence of an acid-binding agent, after which the compound obtained may or may not be converted to an addition salt with a physiologically acceptable acid.

The leaving group B is preferably a halogen, especially chlorine, bromine or iodine. However, it may also be an aliphatic or aromatic sulfonic acid radical, especially the radical of methanesulfonic acid, p-toluenesulfonic acid or benzenesulfonic acid.

The reactions are carried out at room temperature or above, advantageously at from 50° to 120° C. They may be carried out under atmospheric pressure or in a closed vessel under superatmospheric pressure, where necessary with heating to the stated temperature range.

The starting compounds may be reacted directly, ie. without addition of a diluent or solvent. Advantageously, however, the reactions are carried out in the presence of an inert diluent or solvent, for example a lower alcohol of 1 to 4 carbon atoms, eg. methanol, ethanol or a propanol, preferably isopropanol or ethanol, a lower saturated dialkyl ether, dialkyl glycol ether or cyclic ether, eg. diethyl ether, 1,2-dimethoxyethane, tetrahydrofuran or dioxane, a benzene hydrocarbon, eg. benzene or an alkylbenzene, eg. toluene or xylene, an aliphatic hydrocarbon, eg. hexane, heptane or octane, a lower aliphatic ketone, eg. acetone, methyl ethyl ketone or methyl isobutyl ketone, a dialkylformamide, eg. dimethylformamide or diethylformamide, or dimethylsulfoxide, or in the presence of water, or in a mixture of the above solvents.

The amine of the formula H$_2$N—R, used in excess, may also serve as a diluent or solvent.

Preferred solvents for the reaction of 6-(2,3-epoxy-propoxy)-2,3,4,5-tetrahydro-1H-1-benzazepin-2-one with an amine R—NH$_2$ are lower alcohols, especially ethanol or isopropanol, the reaction preferably being carried out at from 50° to 100° C. and under atmospheric pressure.

For the nucleophilic substitution of a radical B, preferred solvents are lower aliphatic ketones, especially acetone or methyl isopropyl ketone, cyclic ethers, especially tetrahydrofuran or dioxane, or dialkylformamides, eg. dimethylformamide, and preferred temperatures are from 90° to 120° C. The presence of a catalytic amount of sodium iodide or potassium iodide may be advantageous.

It should be mentioned that a mixture of the epoxide with a halohydrin may also be used as the starting compound of the formula (II).

In an advantageous embodiment of the nucleophilic substitution of the radical B by the amine used, the reaction is carried out in the presence of a base as an acid-binding agent. Preferred bases are alkali metal hydroxides, carbonates, bicarbonates and alcoholates, and tertiary organic amines, eg. pyridine or a trialkylamine, eg. trimethylamine or triethylamine. Amongst the alkali metal compounds, those of sodium and potassium are particularly suitable. The base is employed in the stoichiometric amount or in slight excess. It can be advantageous to employ an excess of the amine H$_2$N—R used for the reaction, so that it serves at the same time as an acid-binding agent.

The time required for complete conversion depends on the reaction temperature and is in general from 2 to 15 hours. The reaction product can be isolated in the conventional manner, for example by filtration, or by distilling the diluent or solvent from the reaction mixture. The compound obtained is purified in the conventional manner, for example by recrystallization from a solvent, by conversion to an addition compound with an acid, or by column chromatography.

A starting compound of the formula (II) may be obtained by alkylating 6-hydroxy-2,3,4,5-tetrahydro-1H-1-benzazepin-2-one (III)

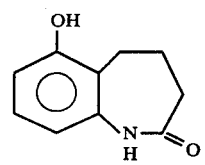

(III)

with an epihalohydrin or an α,ω-dihalo-propan-b 2-ol. Suitable epihalohydrins are epichlorohydrin, epibromohydrin and epiiodohydrin and particularly suitable α,ω-dihalo-propan-2-ols are 1,3-dichloro-propan-2-ol and 1,3-dibromo-propan-2-ol.

The conversion of the 6-hydroxy-2,3,4,5-tetrahydro-1H-1H-1-benzazepin-2-one to a starting compound of the formula (II) is advantageously carried out at from 0° to 120° under atmospheric pressure, or in a closed vessel under superatmospheric pressure. Advantageously, the reaction is carried out in an inert diluent or solvent, for example a lower aliphatic ketone, eg. acetone, methyl ethyl ketone or methyl isobutyl ketone, a lower alcohol of 1 to 4 carbon atoms, eg. methanol, ethanol, propanol or butanol, an aliphatic or cyclic ether, eg. diethyl ether, tetrahydrofuran or dioxane, a dialkylformamide, eg. dimethylformamide or diethylformamide, dimethylsulfoxide or hexamethylphosphorotriamide, or using an excess of the alkylating agent as the diluent or solvent.

The reactions are preferably carried out in the presence of a base as an acid-binding agent. Suitable bases are alkali metal carbonates, bicarbonates, hydroxides, hydrides and alcoholates, especially of sodium and potassium, basic oxides, eg. aluminum oxide or calcium oxide, organic tertiary bases, eg. pyridine or lower trialklamines, eg. trimethylamine or triethylamine. The bases may be used in catalytic amounts or in the stroichiometric amount, or in slight excess, relative to the alkylating agent employed.

Preferably, 6-hydroxy- 2,3,4,5-tetrahydro-1H-1-benzazepin-2-one is reacted with epibromohydrin or 1,2-dibromopropan-2-ol in a solvent mixture comprising an ether and a polar aprotic solvent, especially tetrahydrofuran and hexamethylphosphorotriamide, at from 0° to 50° C., or in acetone at the boil.

According to a further method of preparation, a compound of the general formula (I) may be obtained by alkylating 6-hydroxy-2,3,4,5-tetrahydro-1H-1-benzazepin-2-one in the conventional manner with a compound of the general formula (IV) or (V)

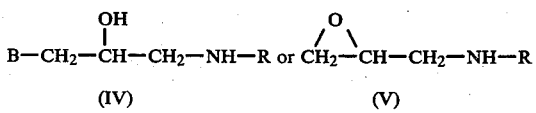

where B and R have the above meanings, advantageously in the presence of a solvent, and in the presence or absence of an acid-binding agent, at from 40° to 120° C. This reaction can be carried out, for example, in accordance with the conditions described in Swiss Pat. No. 451,115 or in German Laid-Open Application DOS No. 2,007,751.

The alkylation of 6-hydroxy-2,3,4,5-tetrahydro-1H-1-benzazepin-2-one with a compound of the formula (IV) is preferably carried out in the presence of an acid-binding agent, eg. an alkali metal hydroxide, carbonate, bicarbonate or alcoholate, or a tertiary organic amine, preferably pyridine or a tertiary aliphatic amine, eg.

trimethylamine or triethylamine. Amongst the alkali metal compounds, those of sodium and potassium are particularly suitable. The base is employed in the stoichiometric amount or in slight excess. Alternatively, the starting compound may be employed in the form of an alkali metal salt, eg. the sodium salt or potassium salt.

The alkylation may be carried out in the presence or absence of a catalytic amount of an amine.

Advantageously, the alkylation reactions are carried out in an inert diluent or solvent, for example a lower aliphatic alcohol of 1 to 4 carbon atoms, eg. methanol, ethanol, propanol, isopropanol or a butanol, or a lower aliphatic ketone, eg. acetone, methyl ethyl ketone or methyl isobutyl ketone, or a dialkylformamide, eg. dimethylformamide or diethylformamide, dimethylsulfoxide or hexamethylphosphorotriamide, or a mixture of the above solvents. The reaction is advantageously accelerated, or completed, by application of heat, eg. by heating at from 40° to 120° C., preferably from 80° to 100° C. Amongst the solvents, the lower aliphatic ketones, dialkylformamides and dimethylsulfoxide are preferred.

6-Hydroxy-2,3,4,5-tetrahydro-1H-1-benzazepin-2-one (III), required as the starting compound, may be prepared by ether cleavage of a 6-alkoxy-2,3,4,5-tetrahydro-1H-1-benzazepin-2-one of the general formula (VI)

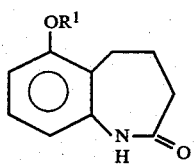

where $R^1$ is alkyl of 1 to 4 carbon atoms or is α-aralkyl.

Examples of alkyl radicals $R^1$ are methyl, ethyl, propyl and butyl, amongst which methyl is preferred. The preferred α-aralkyl radical is benzyl.

The ether cleavage is carried out in the conventional manner with the known conventional reagents for ether cleavage reactions. Amongst these, reagents deserving particular mention are hydrohalic acids, preferably aqueous hydrobromic acid and hydriodic acid, in the presence or absence of red phosphorus and/or of an aliphatic carboxylic acid of 1 to 5 carbon atoms, preferably formic acid or acetic acid, as the diluent or pyridine hydrohalides, for example pyridinium chloride or pyridinium bromide, or lithium iodide in collidine, or diborane or boron trihalides, preferably boron tribromide, in an aromatic hydrocarbon, such as benzene, toluene or xylene, or aluminum chloride in a suitable solvent, for example carbon disulfide or dimethylformamide.

The ether cleavage reactions may be carried out at room temperature or above, for example at from 100° to 150° C., under atmospheric pressure or in a closed vessel under superatmospheric pressure. The reactions may be carried out in an inert solvent or in a melt of the compound which effects the ether cleavage, for example in a pyridinium halide melt or an AlCl$_3$/DMF melt.

The reaction time depends on the reaction temperature and on the reagent employed for the ether cleavage; in general, the cleavage reaction is complete after 5 hours.

The benzyl radical is furthermore preferably removed hydrogenolytically in the presence of a catalyst, for example palladium on a carrier, eg. carbon, aluminum oxide or kieselguhr, in a suitable solvent, for example methanol, ethanol or propanol.

The compounds of the formula (VI), amongst which 6-methoxy-2,3,4,5-tetrahydro-1H-1-benzazepin-2-one is particularly suitable for the preparation of 6-hydroxy-2,3,4,5-tetrahydro-1H-1-benzazepin-2-one (III), are obtainable by conventional methods of enlarging the ring of the corresponding 5-alkoxy-1-tetralones. Suitable ring-enlarging reactions are the Schmidt reaction and the Beckmann rearrangement, as described in Houben-Weyl, Volume 11/2, page 546–554 (Georg Thieme Verlag, Stuttgart; 1958). Specifically, the Schmidt reaction carried out on 1-tetralone is described in detail in J. Chem. Soc. 1937, 456 et seq. and the Beckmann rearrangement via the oxime-benzenesulfonate of 1-tetralone is described in detail in Liebigs Annalen 586 (1954), 30 et seq.

The isomeric 6-alkoxy-2,3,4,5-tetrahydro-1H-2-benzazepin-1-ones, which form in minor amounts, can readily be removed by recrystallization. The structure of the 6-alkoxy-2,3,4,5-tetrahydro-1H-1-benzazepin-2-ones obtained is determined by NMR spectroscopy (cf. also J. Med. Chem. 16 (1973), 516–519).

It should be pointed out that 6-hydroxy-2,3,4,5-tetrahydro-1H-1-benzazepin-2-one can also be prepared directly from 6-hydroxy-tetralone by ring enlargement by the Schmidt reaction, as has been described for 7-hydroxy-2,3,4,5-tetrahydro-1H-1-benzazepin-2-one (J. Med. Chem. 16 (1973), 516–519).

The compounds according to the invention, of the formula (I), have a chirality center on carbon atom 2 of the aliphatic side chain and are obtained as racemates which can be separated into the optically active antipodes by conventional methods, for example by forming diastereomeric salts with optically active auxiliary acids, eg. dibenzoyltartaric acid, camphor-10-sulfonic acid, ditoluyltartaric acid or 3-bromo-camphor-8-sulfonic acid.

The resulting compounds according to the invention may or may not be converted to an acid addition salt with a physiologically acceptable acid. Examples of conventional physiologically acceptable organic or inorganic acids are hydrochloric acid, hydrobromic acid, phosphoric acid and sulfuric acid, amongst inorganic acids, and oxalic acid, maleic acid, fumaric acid, lactic acid, tartaric acid, malic acid, citric acid, salicylic acid, adipic acid and benzoic acid as organic acids; other suitable acids are to be found in Fortschritte der Arzneimittelforschung (Birkhäuser Verlag, Basel and Stuttgart), 10 (1966), 224–225 and J. Pharm. Sci. 66 (1977), 1–5.

The acid addition salts are as a rule obtained in the conventional manner by mixing the free base or a solution thereof with the appropriate acid or a solution thereof in an organic solvent, for example a lower alcohol, eg. methanol, ethanol or propanol, or a lower ketone, eg. acetone, methyl ethyl ketone or methyl isobutyl ketone, or an ether, eg. diethyl ether, tetrahydrofuran or dioxane. To achieve better crystallization, mixtures of the said solvents may also be used. Furthermore, pharmaceutically acceptable aqueous solutions of acid addition compounds of the aminopropanol derivatives of the general formula (I) may be prepared by dissolving a free base of the general formula (I) in an aqueous acid solution.

The compounds according to the invention, of the formula I, and their physiologically acceptable addition salts with acids exhibit valuable pharmacological properties and may be used in cases of cardiac and circulatory disorders. Because of their beta-sympatholytic action, the compounds are particularly suitable for the treatment of coronary cardiac disorders, cardiac arrhythmias and hypertonia.

By way of example, the high β-sympatholytic activity of the novel compounds far surpasses that of the known compound propranolol. This finding is surprising, and was unforeseeable, since the 7-(2-hydroxy-3-alkylaminopropoxy)-2,3,4,5-tetrahydro-1H-2-benzazepin-1-ones (J. Med. Chem. 16 (1973), 516–519) which are isomeric to (I), ie. which are compounds which compared to the compounds according to the invention have the 2-hydroxy-3-alkylamino-propoxy group in the 7-position and in addition have the NH and C=O group interchanged in the benzazepine ring, are only very weak β-sympatholytic agents. The 5-(2-hydroxy-3-alkylamino-propoxy)-3,4-dihydrocarbostyrils (J. Med. Chem. 17 (1974), 529–533), which are similar to (I), also do not reach the activity of the compounds according to the invention.

The β-sympatholytic action was tested on cats and dogs. The comparative compound used was the conventional β-sympatholytic agent propranolol. The isoproterenol-induced tachycardia model was used for the test.

Isoproterenol (1 μg/kg, administered intravenously) produces increases in heart rate averaging 61±2.4 beats/min. in cats (male and female, mongrels, weighing 1.7 to 4.0 kg) narcotized with hexobarbital (200 mg/kg administered intramuscularly). β-Sympatholytic agents inhibit this tachycardia. Isoproterenol was injected before, and 10 minutes after, the intravenous administration, or 30 minutes after the intraduodenal administration, of the test substances. The doses which inhibit the isoproterenol-induced tachycardia by 50–60% were determined.

On conscious dogs, isoproterenol (1 μg/kg administered intravenously) causes an increase in heart rate of about 100 beats/min. β-Sympatholytic agents inhibit this tachycardia. Isoproterenol was administered before and 10 minutes after the intravenous administration of the test substances.

Linear relationships are found between the logarithms of the administered doses (mg/kg) of the test substances and inhibition of the isoproterenol-induced tachycardia (%). From these relationships, the ED 50% ie. the doses which inhibit the isoproterenol-induced tachycardia by 50%, are determined.

In addition to testing the β-sympatholytic action, the acute toxicity for interperitoneal administration was determined on groups of 10 female NMRI mice weighing 22–27 g each. The LD 50 is the calculated dose (Probit analysis) after which 50% of the animals died within 24 hours.

The compounds according to the invention are highly active β-sympatholytic agents. Table 1 shows that the doses required for 50–60% inhibition of isoproterenol-induced tachycardia are, for the pharmacotherapeutically important case of enteral (intraduodenal) administration, lower, in the case of cats, by a factor of 2 (Example 1) or 4.7 (Example 2) than the corresponding dose of propranolol.

For intravenous administration, the doses required are lowered by a factor of 4.7 (Example 2) or a factor of 2 (Example 1) than in the case of propranolol.

The high β-sympatholytic activity of the compound of Example 2 can also be ascertained in dogs. The ED 50% is found to be 0.0043 mg/kg, so that the substance is 24 times as active as propranolol (ED 50%=0.10 mg/kg).

The toxicity of the compound of Example 2 is less than that of propranolol. The LD 50 for intraperitoneal administration to mice is 237 mg/kg whilst that of propranolol is 108 mg/kg.

TABLE 1

| | β-Sympatholytic action in cats | | | |
|---|---|---|---|---|
| | Isoproterenol-induced tachycardia | | | |
| | Intravenous administration | | Intraduodenal administration | |
| Example No. | mg/kg | %[1] | mg/kg | %[1] |
| 1 | 0.215 | 59 | 0.464 | 56 |
| 2 | 0.0215 | 57 | 0.215 | 52 |
| Propranolol | 0.1 | 52 | 1.0 | 57 |

[1]% inhibition

Accordingly, the present invention also relates to therapeutic agents or formulations which in addition to conventional carriers and diluents contain a compound of the formula I as the active compound, and to the use of the novel compounds for therapeutic purposes.

The chemotherapeutic agents or formulations are prepared in the conventional manner, employing a suitable dosage of the active compound, and using the conventional carriers or diluents and the conventional pharmaceutical auxiliaries, appropriate to the desired route of administration.

The preferred formulations are those suitable for oral administration. Examples of these are tablets, film tablets, dragees, capsules, pills, powders, solutions or suspensions, or depot forms.

Of course, formulations for parenteral administration, eg. injection solutions, may also be used. Further examples of suitable formulations are suppositories.

Appropriate tablets may be prepared, for example, by mixing the active compound with conventional auxiliaries, for example inert diluents, eg. dextrose, sucrose, sorbitol, mannitol, polyvinylpyrrolidone, calcium carbonate, calcium phosphate or lactose, disintegrating agents, eg. corn starch or alginic acid, binders, eg. starch or gelatin, lubricants, eg. magnesium stearate or talc, and/or agents for achieving a depot effect, eg. carboxypolymethylene, carboxymethylcellulose, cellulose acetate-phthalate or polyvinyl acetate. The tablets may also consist of several layers.

Similarly, dragees may be prepared by coating cores, themselves prepared similarly to the tablets, with agents conventionally employed for dragee coating, for example collidone or shellac, gum arabic, talc, titanium dioxide or sugar. The dragee coating may also consist of several layers, in which case the auxiliaries mentioned above in connection with tablets may be used.

Solutions or suspensions containing the active compounds according to the invention may additionally contain flavor-improving agents, eg. saccharin, cyclamate or sugar, as well as, for example, aromatics, eg. vanillin or orange extract. In addition they may contain suspending agents, eg. sodium carboxymethylcellulose, or preservatives, eg. p-hydroxybenzoates. Capsules containing the active compound may be prepared, for example, by mixing the latter with an inert carrier, eg. lactose or sorbitol, and enclosing the mixture in gelatin capsules.

Suitable suppositories may be prepared, for example, by mixing the active compound with appropriate suppository bases, eg. neutral fats or polyethylene glycol or derivatives thereof.

For man, suitable individual doses of a compound according to the invention are from 0.5 to 50 mg, preferably from 1 to 10 mg.

The Examples which follow illustrate the present invention.

PREPARATION OF STARTING COMPOUNDS

EXAMPLE Ia

6-Hydroxy-2,3,4,5-tetrahydro-1H-1-benzazepin-2-one ($AlCl_3$/dimethylformamide cleavage)

10 ml of DMF are added to 65 g of anhydrous aluminum chloride with vigorous stirring, and cooling if necessary. 13.5 g (0.07 mole) of 6-methoxy-2,3,4,5-tetrahydro-1H-1-benzazepin-2-one are introduced in portions into the resulting melt, and the contents of the flask are then heated to 110°–140° C., left at this temperature for 10 minutes, and thereafter stirred for a further 30 minutes without additional heating. The contents of the flask are then poured into ice water, the sand-colored precipitate formed is filtered off and the filtrate is re-extracted repeatedly with ether. The ether phases are combined, dried and concentrated on a rotary evaporator. The residue is recrystallized from an acetone/cyclohexane/ethyl acetate mixture in the presence of animal charcoal. 6.3 g of 6-hydroxy-2,3,4,5-tetrahydro-1H-1-benzazepin-2-one (51% yield), of melting point 244°–245° C., are obtained.

$C_{10}H_{11}NO_2$ (177.2) Calculated C 68.7%; H 7.3%; N 7.3%. Found C 68.5%; H 7.1%; N 7.2%.

EXAMPLE Ib

6-Hydroxy-2,3,4,5-tetrahydro-1H-1-benzazepin-2-one (pyridinium chloride cleavage)

3.8 g (0.02 mole) of 6-methoxy-2,3,4,5-tetra-hydro-1H-1-benzazepin-2-one and 10 g of pyridinium chloride are heated for 2 hours at 200°–220° C. The melt is cooled and poured into water, and the mixture is acidified with 2 N $H_2SO_4$ and extracted repeatedly with ether. The combined organic phases are dried and concentrated and the residue is recrystallized from an acetone/cyclohexane/ethyl acetate mixture in the presence of animal charcoal. 1.6 g of 6-hydroxy-2,3,4,5-tetrahydro-1H-1-benzazepin-2-one, of melting point 243°–244° C., are obtained. This material is identical with the product obtained under Ia.

EXAMPLE II

6-Methoxy-2,3,4,5-tetrahydro-1H-1-benzazepin-2-one 9.7 g (0.029 mole) of 5-methoxy-tetralone-1-oxime benzenesulfonate in 800–900 ml of 50% strength acetic acid are kept on a waterbath until completely dissolved (about 60 minutes). The solution is then diluted with twice its volume of water and the mixture is repeatedly extracted with ether. The combined ether extracts are washed first with aqueous bicarbonate solution and then repeatedly with water, and are dried and concentrated. The residue which remains crystallizes on being left to stand, and is analytically pure. 4.2 g of 6-methoxy-2,3,4,5-tetrahydro-1H-1-benzazepin-2-one (75.7% yield), of melting point 162° C., are obtained.

$C_{11}H_{13}NO_2$ (191.2) Calculated: C 69.0%; H 6.8%; N 7.3%. Found: C 68.8%; H 6.9%; N 7.2%.

EXAMPLE III

5-Methoxy-tetralone-1-oxime benzenesulfonate 10 g (0.042 mole) of tetralone-1-oxime are dissolved in 80 ml of anhydrous pyridine. 10.8 g of benzenesulfonic acid chloride are added dropwise in the course of 15 minutes at room temperature and the solution is left to stand for 12 hours. 5 ml of water are then added, after which the solution is poured into 300 ml of ice-cold 4 N HCl. The resulting precipitate is filtered off, dried and recrystallized from ethanol. 13.6 g (92.8% yield) of 5-methoxy-tetralone-1-oxime benzenesulfonate, of melting point 142°–144° C., are isolated.

$C_{17}H_{17}NO_4S$ (331): Calculated: C 61.6%; H 5.2%; N 4.2%; S 9.6%. Found: C 61.7%; H 5.3%; N 4.3%; S 9.7%.

EXAMPLE IV

5-Methoxy-tetralone-1-oxime 17.7 g (0.1 mole) of commercial 5-methoxy-1-tetralone (from Aldrich), 18.4 g (0.26 mole) of hydroxylamine hydrochloride and 22.6 g of sodium bicarbonate (0.26 mole), in 450 ml of methanol and 80 ml of water, are refluxed for 36 hours. The solvent is then removed on a rotary evaporator, the residue is thoroughly stirred with water and the precipitate is filtered off, dried and recrystallized from toluene. 15.2 g of 5-methoxy-tetralone-1-oxime (79.6% yield), of melting point 158°–159° C., are obtained.

$C_{11}H_{13}NO_2$ (191.2) Calculated: C 69.0%; H 6.8%; N 7.3%. Found: C 69.1% ; H 6.6%; N 7.1%.

EXAMPLE V 6-(2,3-Epoxy-propoxy)-2,3,4,5-tetrahydro-1H-1-benzazepin-2-one 5.3 g (0.03 mole) of 6-hydroxy-2,3,4,5-tetrahydro-1H-benzazepin-2-one, 5 ml of epibromohydrin and 4.5 g of potassium carbonate in 250 ml of methyl isobutyl ketone are refluxed for 48 hours. After the mixture has cooled, it is filtered and the filtrate is concentrated under reduced pressure on a rotary evaporator. The residue is recrystallized from cyclohexane in the presence of animal charcoal. 4.2 g (60% yield) of 6-(2,3-epoxy-propoxy)-2,3,4,5-tetrahydro-1H-1-benzazepin-2-one, of melting point 121°–123° C., are obtained.

$C_{13}H_{15}NO_3$ (233) Calculated: C 66.9%; H 6.5%; N 6.0%. Found: C 66.6%; H 6.6%; N 5.8%.

Preparation of the compounds according to the invention

EXAMPLE 1

6-(2-Hydroxy-3-isopropylaminopropoxy)-2,3,4,5-tetrahydro-1H-1-benzazepin-2-one 3.3 g (0.014 mole) of 6-(2,3-epoxypropoxy)-2,3,4,5-tetrahydro-1H-1-benzazepin-2-one are dissolved in 400 ml of n-propanol, 3 g of isopropylamine are added and the mixture is kept on a boiling waterbath for from 4 to 6 hours. The solvent and excess amine are then distilled off on a rotary evaporator and the residue is twice taken up in methanol, the solvent again being distilled off. The residue thus obtained is chromatographed on a silica gel column, using methanol as the mobile phase. 1.65 g (39.9% yield) of 6-(2-hydroxy-3-isopropylaminopropoxy)-2,3,4,5-tetrahydro-1H-1-benzazepin-2-one, of melting point 143°–145° C., are obtained.

$C_{16}H_{24}N_2O_3$ (292) Calculated: C 65.7%; H 8.3%; N 9.6%. Found: C 65.4%; H 8.4%; N 9.4%.

EXAMPLE 2

6-(2-Hydroxy-3-tert.-butylaminopropoxy)-2,3,4,5-tetrahydro-1H-1-benzazepin-2-one hydrochloride Following the procedure described in Example 1, 9.4 g (0.04 mole) of 6-(2,3-epoxypropoxy)-2,3,4,5-tetrahydro-1H-1-benzazepin-2-one are reacted with 5.8 g of tert.-butylamine. The compound is precipitated as the hydrochloride from an ethanol/acetone mixture by means of a solution of HCl in ether, and the hydrochloride is then recrystallized from an ethanol-/acetone/ether mixture. 3.6 g (26.2% yield) of 6-(2-hydroxy-3-tert.-butylaminopropoxy)-2,3,4,5-tetrahydro-1H-1-benzazepin-2-one hydrochloride, of melting point 202° C., are obtained.

$C_{17}H_{27}N_2O_3Cl$ (342.5) Calculated: C 59.6%; H 7.9%; N 8.2%; Cl 10.4%. Found: C 59.6%; H 8.2%; N 7.6%; Cl 10.1%.

EXAMPLE 3

6-(2-Hydroxy-3-sec.-butylaminopropoxy)-2,3,4,5-tetrahydro-1H-1-benzazepin-2-one hydrochloride 1.7 g (0.007 mole) of 6-(2,3-epoxypropoxy)-2,3,4,5-tetrahydro-1H-1-benzazepin-2-one and 2.5 g of 2-aminobutane are reacted by the method described in Example 1 and the product is isolated as the hydrochloride by the method described in Example 2. 1.05 g (42% yield) of 6-(2-hydroxy-3-sec.-butylaminopropoxy)-2,3,4,5-tetrahydro-1H-1-benzazepin-2-one hydrochloride, of melting point 177° C., are obtained.

$C_{17}H_{27}N_2O_3Cl$ (342.5) Calculated: C 59.6%; H 7.9%; N 8.2% ; Cl 10.4%. Found: C 59.3% ; H 8.1% ; N 7.7%; Cl 10.2%.

EXAMPLE 4

6-[2-Hydroxy-3-(3-methyl-but-1-yn-3-ylamino)-propoxy]-2,3,4,5-tetrahydro-1H-1-benzazepin-2-one hydrochloride 1.7 g (0.007 mole) of 6-(2,3-epoxypropoxy)-2,3,4,5-tetrahydro-1H-1-benzazepin-2-one and 1.25 g of 3-amino-3-methyl-but-1-yne are reacted by the method of Example 1. 0.85 g (33% yield) of 6-[2-hydroxy-3-(3-methyl-but-1-yn-3-ylamino)-propoxy]-2,3,4,5-tetrahydro-1H-1-benzazepin-2-one hydrochloride, of melting point 177° C., is obtained.

$C_{18}H_{25}N_2O_3Cl$ (352.5) Calculated: C 61.3%; H 7.1%; N 7.9%; Cl 10.1%. Found: C 61.2%; H 7.3%; N 7.7%; Cl 10.3%.

There follow examples of formulations which are prepared in the conventional manner:

| 1 Tablets | |
|---|---|
| (a) An active compound of the formula I | 5 mg |
| Lactose | 200 mg |
| Methylcellulose | 15 mg |
| Corn starch | 50 mg |
| Talc | 11 mg |
| Magnesium stearate | 4 mg |
| | 285 mg |
| (b) An active compound of the formula I | 10 mg |
| Lactose | 188 mg |
| Avicel | 80 mg |
| Polywachs 6000 | 20 mg |
| Magnesium stearate | 2 mg |
| | 300 mg |
| (c) An active compound | |

| 1 Tablets | |
|---|---|
| of the formula I | 10 mg |
| Polyvinylpyrrolidone (mean molecular weight 25,000) | 210 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 280 mg |

The active compound is moistened with a 10% strength aqueous solution of the polyvinylpyrrolidone, forced through a sieve of 1.0 mm mesh width and dried at 50° C. The resulting granules are mixed with polyethylene glycol (mean molecular weight 4,000), hydroxypropylmethylcellulose, talc and magnesium stearate, and the mixture is pressed to give tablets each weighing 280 mg.

| 2. Example of dragees | |
|---|---|
| A compound of the formula I | 2.5 mg |
| Lactose | 90.5 mg |
| Corn starch | 60 mg |
| Polyvinylpyrrolidone | 6 mg |
| Magnesium stearate | 1 mg |
| | 160.0 mg |

The mixture of the active compound with lactose and corn starch is moistened with an 8% strength aqueous solution of the polyvinylpyrrolidone and granulated by passing through a sieve of 1.5 mm mesh width, dried at 50° C. and again forced through a sieve, this time of 1.0 mm mesh width. The granules obtained are mixed with magnesium stearate and the mixture is pressed to form dragee cores. These are then coated in the conventional manner with a coating essentially consisting of sugar and talc.

| 3. Capsule formulation | | |
|---|---|---|
| A compound of the formula I | 5.0 | mg |
| Magnesium stearate | 2.0 | mg |
| Lactose | 19.3 | mg |

| 4. Injection solution | | |
|---|---|---|
| A compound of the formula I | 1.0 | mg |
| Sodium chloride | 9 | mg |
| distilled water to make up to 1.0 ml | | |

We claim:
1. A compound of the formula (I)

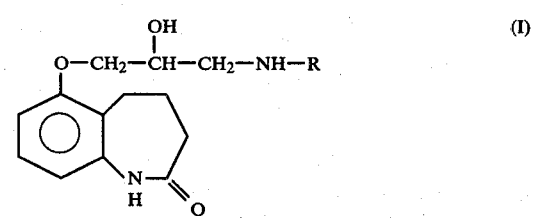

where R is alkyl of 3 to 6 carbon atoms, which is branched at the carbon adjacent to the amino nitrogen, but-3-yn-2-yl or 3-methyl-but-1-yn-3-yl, and its physiologically acceptable addition salts with acids.

2. 6-(2-Hydroxy-3-isopropylaminopropoxy)-2,3,4,5-tetrahydro-1H-1-benzazepin-2-one.

3. 6-(2-Hydroxy-3-sec.-butylaminopropoxy)-2,3,4,5-tetrahydro-1H-1-benzazepin-2-one.

4. A therapeutic agent having β-sympatholytic activity which comprises: a pharmacologically acceptable carrier and/or diluent and a therapeutically effective amount of a compound of the formula I as described in claim 1.